(12) United States Patent
Böttcher et al.

(10) Patent No.: US 6,350,714 B1
(45) Date of Patent: Feb. 26, 2002

(54) METHOD FOR PREPARING A CATALYST AND CATALYSTS PREPARED ACCORDINGLY

(75) Inventors: Arnd Böttcher, Frankenthal; Jochem Henkelmann, Mannheim; Thomas Preiss, Ludwigshafen; Melanie Brunner, Schifferstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/555,603

(22) PCT Filed: Dec. 1, 1998

(86) PCT No.: PCT/EP98/07785

§ 371 Date: May 31, 2000

§ 102(e) Date: May 31, 2000

(87) PCT Pub. No.: WO98/35863

PCT Pub. Date: Aug. 20, 1998

(51) Int. Cl.⁷ .......................... B01J 31/00; B01J 21/18; B01J 23/02; C07C 209/00; C07C 215/00; C07C 31/18; C07C 27/00

(52) U.S. Cl. .................. 502/108; 502/154; 502/174; 502/344; 502/345; 564/471; 564/487; 564/503; 568/855; 568/865

(58) Field of Search ................................. 502/108, 174, 502/344, 345, 154; 564/471, 503, 487; 568/865, 855

(56) References Cited

U.S. PATENT DOCUMENTS

| | | | |
|---|---|---|---|
| 3,462,507 A | 8/1969 | Kahn | 260/665 |
| 3,496,232 A | 2/1970 | Tedeschi et al. | 260/583 |
| 3,560,576 A | 2/1971 | Kirchner | 260/635 |
| 3,650,985 A | 3/1972 | Kirchner | 252/431 |
| 3,957,888 A | 5/1976 | Reiss et al. | 260/635 |
| 4,093,668 A | 6/1978 | Reiss et al. | 568/855 |
| 4,110,249 A | 8/1978 | Fremont | 252/431 |
| 4,119,790 A | 10/1978 | Hort | 568/855 |
| 4,127,734 A | 11/1978 | Fremont | 568/855 |
| 4,387,042 A | 6/1983 | Hort et al. | 252/392 |
| 4,536,491 A | 8/1985 | Fremont | 502/174 |
| 4,584,418 A | 4/1986 | Fremont | 568/855 |
| 5,808,160 A * | 9/1998 | Ruhl et al. | 564/503 |
| 5,840,986 A * | 11/1998 | Preiss et al. | 564/471 |

FOREIGN PATENT DOCUMENTS

| | | |
|---|---|---|
| DE | 2602-418 | 7/1977 |
| GB | 968 928 | 9/1964 |

* cited by examiner

*Primary Examiner*—Johann Richter
*Assistant Examiner*—Elvis O. Price
(74) *Attorney, Agent, or Firm*—Keil & Weinkauf

(57) ABSTRACT

The present invention relates to a process for preparing a catalyst by activating a catalytic composition which comprises a) at least one metal of group IB or IIB or a compound thereof, b) where appropriate a carrier which comprises treating the composition with an alkyne of the general formula I $$R^1\!-\!C\!\equiv\!C\!-\!R^2 \qquad (I)$$

in which $R^1$ is alkyl, cycloalkyl, aryl, hydroxyalkyl, haloalkyl, alkoxy or alkoxyalkyl, $R^2$ is a hydrogen atom, alkyl, cycloalkyl or aryl, and a carbonyl compound of the general formula II $$O\!=\!C\!\begin{smallmatrix}R^3\\R^4\end{smallmatrix} \qquad (II)$$

in which $R^3$ and $R^4$ are, independently of one another, a hydrogen atom, alkyl, haloalkyl, cycloalkyl or aryl, to catalysts obtainable by this process, and to alkynylations and aminoalkylations employing these catalysts.

12 Claims, No Drawings

METHOD FOR PREPARING A CATALYST AND CATALYSTS PREPARED ACCORDINGLY

This is the National Phase Application of PCT/EP98/07785, filed Dec. 01, 1998.

The present invention relates to a process for preparing a catalyst by activating a catalytic composition which comprises at least one compound of a metal of group IB or IIB of the Periodic Table, where appropriate bismuth or a compound thereof, and where appropriate a carrier, and to the catalysts obtainable by this process. The invention further relates to a process for preparing alkynols and to a process for preparing aminoalkynes using these catalysts.

The preparation of alkynols by addition of a carbonyl compound onto an alkyne and, in particular, onto acetylene with retention of the triple bond, and the preparation of aminoalkynes by reacting an alkyne with a carbonyl compound and an amine in a Mannich-type condensation have been known for a long time and used industrially. Both reactions can be catalyzed homogeneously or heterogeneously, generally employing heavy metal acetylides and, in particular, catalysts based on copper(I) acetylide.

U.S. Pat. No. 3,496,232 describes the preparation of N-alkyl-substituted aminoalkynes in a homogeneously or heterogeneously catalyzed Mannich reaction, the catalysts employed being salts of metals of group IB or IIB, such as, for example, the chlorides, acetates, formates and acetylides and, specifically, copper acetylide. These can, in the case of the heterogeneously catalyzed process variant, be employed on an inert carrier. The copper acetylide catalyst is prepared in this case before the actual Mannich reaction by reacting copper(II) chloride with paraformaldehyde and acetylene in an autoclave.

DE-A-23 14 693 describes a process for preparing butynediol by reacting acetylene and formaldehyde, employing a supported heavy metal acetylide catalyst which is obtained by impregnating a carrier with a heavy metal salt solution and subsequently treating with gaseous acetylene.

DE-A-24 21 407 likewise describes a process for preparing butynediol, employing supported copper acetylide catalysts.

DE-A-26 02 418 describes a process for preparing butynediol, employing a supported catalyst which is obtained by reacting a copper(II) compound with acetylene and formaldehyde in aqueous solution at a pH below 5.5.

U.S. Pat. No. 3,650,985 describes the prepartion of unsupported copper acetylide catalysts of the general formula $(CuC_2)_w(CH_2O)_x(C_2H_2)_y(H_2O)_z$ with $1 \leq w$, $x$, $y<100$, preferably $w=4$, $x=0.24$ to 4, $y=0.24$ to 4 and $z=0.67$ to 2.8. These catalysts may additionally contain a bismuth compound and can be prepared by formaldehyde and acetylene acting simultaneously on the particulate, water-insoluble copper compound, preferably basic copper carbonate, such as, for example, synthetically prepared malachite. They are used as aqueous catalyst suspension for the ethynylation of acetylenically unsaturated hydrocarbons. Similar malachite catalysts are described in U.S. Pat. No. 3,560,576.

U.S. Pat. No. 4,110,249 describes a process for preparing bismuth-modified spheroidal malachites and their reaction with acetylene and formaldehyde to give unsupported ethynylation catalysts. U.S. Pat. No. 4,127,734 describes a process for preparing 1,4-butynediol by reacting acetylene and formaldehyde in the presence of these catalysts.

U.S. Pat. No. 4,536,491 describes agglomerates of spheroidal malachites which comprise bismuth and silica. These malachites can be converted into copper acetylide complexes by reacting in the form of an aqueous suspension with acetylene and formaldehyde. U.S. Pat. No. 4,584,418 describes a process for preparing 1,4-butynediol by reacting acetylene with formaldehyde in the presence of these catalysts.

U.S. Pat. No. 4,119,790 describes a continuous, multistage low-pressure ethynylation process for preparing 1,4-butynediol, employing an ethynylation catalyst based on a water-insoluble copper acetylide complex. This ethynylation catalyst is prepared by reacting a precursor which comprises between 20 and 35% by weight of copper and 0 to 3% by weight of bismuth on a magnesium silicate carrier with formaldehyde in the presence of acetylene.

EP-A-0 080 794 describes a heterogeneously catalyzed process for preparing N,N-disubstituted propynylamines, the catalysts employed being copper acetylides on a magnesium silicate carrier doped with bismuth oxide. These are conventional ethynylation catalysts which must be activated before they are used with acetylene and formaldehyde.

The disadvantage of the catalysts described above is that they are prepared by activating a catalytic composition using acetylene. Operations with acetylene, which is a thermally unstable gas which easily explodes even under atmospheric pressure, are industrially complicated because considerable safety measures are necessary in the design of the reactors. This particularly applies to operations with liquefied acetylene and/or manipulation thereof under high pressures. The heavy metal catalysts obtained on activation of the catalytic composition with acetylene are also generally prone to explosive decomposition and can therefore be manipulated only with difficulty. Processes in which catalysts of these types are employed are therefore at a commercial disadvantage. This particularly applies when acetylene is employed only in the preparation or activation of the catalyst, while the subsequent ethynylation or aminoalkylation reaction takes place with use of a different alkyne.

It is an object of the present invention to provide a process for preparing a catalyst by activating a catalytic composition allowing the use of acetylene to be dispensed with.

We have found that this object is achieved by a process in which a catalytic composition which comprises at least one metal of group IB or IIB of a compound thereof, where appropriate bismuth or a compound thereof, and where appropriate a carrier, is activated with an alkyne different from acetylene and with a carbonyl compound.

It has also been found, surprisingly, that the use of acetylene in activating the catalytic composition can generally also be dispensed with if the following alkynylation or aminoalkylation reaction is carried out in the presence of acetylene, because the alkyne employed for the activation can generally be different from the alkyne employed for the following reaction.

The invention therefore relates to a process for preparing a catalyst by activating a catalytic composition which comprises
 a) at least one metal of group IB or IIB or a compound thereof,
 b) where appropriate a carrier
which comprises treating the composition with an alkyne of the general formula I

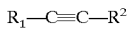 (I)

in which
 $R^1$ is alkyl, cycloalkyl, aryl, hydroxyalkyl, haloalkyl, alkoxy or alkoxyalkyl, $R^2$ is a hydrogen atom, alkyl, cycloalkyl or aryl, and a carbonyl compound of the general formula II

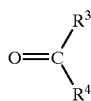
(II)

in which
$R^3$ and $R^4$ are, independently of one another, a hydrogen atom, alkyl, haloalkyl, cycloalkyl or aryl.

For the purpose of the present invention, halogen is fluorine, chlorine, bromine and iodine and, in particular, chlorine and bromine.

The term "alkyl" comprises straight-chain and branched alkyl groups. These are preferably straight-chain or branched $C_1$–$C_{12}$-alkyl and, in particular, $C_1$–$C_6$-alkyl groups. Examples of alkyl groups are, in particular, methyl, ethyl, propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 1-ethylpentyl, 2-ethylpentyl, 1-propylbutyl, octyl, decyl and dodecyl.

Haloalkyl is an alkyl group as defined above which is halogenated with one or more halogen atoms, in particular chlorine and bromine, partially or completely, preferably with one to three halogen atoms.

The above statements about the alkyl group and haloalkyl group apply in a corresponding manner to the alkyl group in alkoxy, alkoxyalkyl and hydroxyalkyl radicals.

Cycloalkyl is preferably $C_3$-$C_8$-cycloalkyl such as cyclopropyl, cyclobutyl, cyclopentyl, cyclohexyl, cycloheptyl or cyclooctyl, or cyclopentylmethyl, cyclopentylethyl and cyclohexylmethyl and cyclohexylethyl.

Aryl is preferably phenyl or naphthyl.

The catalytic composition preferably used in the process according to the invention comprises copper or a copper compound as component a). Suitable copper compounds a) are selected, for example, from copper halides such as copper(I) chloride, copper(II) chloride, copper(I) bromide and copper(II) bromide, copper(I) sulfate, copper(II) sulfate, copper(II) hydroxide, copper (I) oxide, copper(II) oxide, copper phosphates, copper silicates, basic copper carbonates etc., and mixtures thereof. Preferred copper compounds a) are copper(II) oxide and basic copper carbonates such as natural and, particularly preferably synthetic malachites.

Suitable bismuth compounds are selected, for example from bismuth oxide $Bi_2O_3$, bismuth subcarbonate $(BiO)_2CO_3$, bismuth nitrate $Bi(NO_3)_3$ and bismuth subnitrate $BiO(NO_3)$. Bismuth oxide is preferably employed as component b).

The catalytic compositions employed for the activation in the process according to the invention may, where appropriate, comprise a carrier c) which is selected, in particular, from alumina, aluminosilicates, zirconium oxide, titanium dioxide and, preferably, silica.

The catalytic composition employed for the activation preferably comprises 10 to 20% by weight of copper(II) oxide, 1 to 5% by weight of bismuth oxide and 75 to 89% by weight of silica as carrier.

Supported catalytic compositions suitable for the activation are known in the art and are described, for example, in U.S. Pat. No. 3,650,985, DE-A-26 02 418 and U.S. Pat. No. 4,119,790. The disclosure of these publications is incorporated herein by reference, although the activation of the supported catalytic compositions described therein takes place without use of acetylene in the process according to the invention.

In a preferred embodiment of the present invention, an unsupported catalytic composition which comprises a Bi-doped malachite is employed for the activation. Catalytic compositions of this type are described, for example in U.S. Pat. No. 4,110,249, DE-A-25 08 084 and U.S. Pat. No. 4,536,491. The disclosure of these publications is likewise incorporated herein by reference, although the activation of the unsupported catalytic compositions described therein once again takes place without use of acetylene in the process according to the invention.

For the activation, the supported or unsupported catalytic compositions described above are treated with an alkyne of the general formula I and a carbonyl compound of the general formula II. The temperature during this is generally in a range from about 0 to 150° C., preferably about 20 to 100° C. The pH of the reaction medium employed for treating the catalytic compositions is generally in the acid or neutral range such as, for example, at pH values from about 4.0 to 7.0, preferably in the slightly acidic range such as, for example, at pH values from about 5.5 to 6.9. The pH can be adjusted by employing conventional bases such as alkali metal hydroxides, e.g. NaOH and KOH, alkali metal carbonates, e.g. $Na_2CO_3$ and $K_2CO_3$, and alkali metal bicarbonates, e.g. $NaHCO_3$ and $KHCO_3$. The catalytic composition is preferably activated as suspension in water. However, it is also possible to employ mixtures of water and at least one completely water-miscible organic solvent which is inert toward the reactants. Examples of suitable solvents are saturated cyclic ethers, such as tetrahydrofuran and dioxane.

The pressure during the activation of the catalytic compositions is generally lower than in processes known in the art in which acetylene is employed for the activation. The pressure in the process according to the invention is generally up to about 3 bar, preferably up to about 2 bar. In a particularly preferred embodiment, the activation of the catalytic compositions takes place under atmospheric pressure.

If the alkyne of the general formula I employed is an alkyne which is gaseous under the reaction conditions, such as, for example, propyne or butyne, the activation can, if required, be carried out under autogenous pressure while maintaining the pressure conditions described above. In a possible reaction procedure, the carbonyl compound of the general formula II can then be introduced together with the unsupported or supported catalytic composition and, where appropriate, with a solvent into a reactor equipped with a mixing apparatus. Suitable reactors are known to the skilled worker. They include the reaction vessels described in Ullmanns Enzyklopadie der technischen Chemie, 3rd edition, volume 1, page 117 ff. and page 769 ff. (1951) for reactions under pressure. Addition of the gaseous alkyne preferably takes place below the level of the liquid activation mixture introduced, e.g. with an immersion pipe or a coiled pipe having orifices in or opposite to the direction of flow of the reaction mixture. The rate of addition is limited by the abovementioned pressure ranges to be maintained.

If the alkyne of the general formula I employed is liquid or solid under the reaction conditions, the activation can generally take place under atmospheric pressure in a reactor customary for this purpose and having a mixing apparatus, e.g. in a stirred reactor. The activation can then take place, for example, in a batch procedure, in which case the carbonyl compound is preferably introduced into the reactor with a suspension of the unsupported or supported catalytic composition in water and, where appropriate, a solvent, and the alkyne is fed, undiluted or as solution, into the reactor as it is consumed.

In a preferred embodiment of the process according to the invention, the catalytic compositions are activated by employed alkynes of the formula I in which the radical $R^1$ is alkyl or hydroxyalkyl. The radical $R^2$ is preferably a hydrogen atom or alkyl. Examples thereof include propyne, 1-butyne, 1-pentyne, 1-hexyne, 1-heptyne, 1-octyne, propynol, 3-butyn-1-ol, 3-butyn-2-ol, 2-methyl-3-butyn-2-ol, 4-pentyn-1-ol, 4-pentyn-2-ol, 4-pentyn-3-ol, 2-methyl-4-pentyn-2-ol, 3-methyl-4-pentyn-2-ol, 3-methyl-4-pentyn-3-ol etc. Those preferably employed are 3-butyn-2-ol, 2-methyl-3-butyn-2-ol and 1-hexyne.

In a preferred embodiment of the process according to the invention, the catalytic compositions are activated by employing carbonyl compounds of the general formula II in which $R^3$ and $R^4$ are, independently of one another a hydrogen atom or alkyl. Examples thereof include acetaldehyde, propionaldehyde, n-butyraldehyde, n-valeraldehyde etc. Formaldehyde or a condensate thereof, e.g. paraformaldehyde, is particularly preferably employed.

The process according to the invention is suitable not only for preparing a catalyst by activation of a catalytic composition but also, advantageously, for reactivating a previously used, deactivated catalyst.

The invention further relates to the catalysts which are obtainable by the process described above. It is possible in the preparation of these catalysts by the process according to the invention to dispense with activation of the catalytic compositions with acetylene. This is particularly advantageous when the resulting catalyst is to be employed in a process in which acetylene is likewise not used as reactant. It is thus generally possible to make such processes more economic using the catalysts according to the invention because it is possible to dispense with the safety measures needed for operations with acetylene. This is particularly true when no gaseous alkynes are employed for activating the catalytic compositions, so that this can be carried out under atmospheric pressure. In contrast to the copper acetylides employed to date as catalysts, the catalysts according to the invention are generally not prone to explosive decomposition either, and can thus be manipulated without hazard. The activity of these catalysts is generally at least comparable to that of catalysts activated with acetylene. Particularly for the alkynylation of alkynes or hydroxyalkynes with terminal triple bonds the catalysts according to the invention generally show an activity which is as good as or better than corresponding catalysts activated with acetylene. This also applies specifically to ethynylation reactions using acetylene. Even if, as in this case, acetylene is employed for the catalyzed reaction, it is advantageous to employ an alkyne different from acetylene for activating the catalyst. As described above, the catalysts according to the invention are generally not prone to explosive decompositions and can thus be manipulated and stored more easily. The safety precautions necessary for operations with acetylene are thus dispensed with at least for the activation of the catalytic compositions.

The invention further relates to a process for preparing alkynols of the general formula III

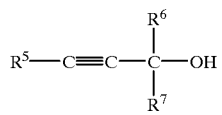

in which $R^5$ is a hydrogen atom, alkyl, haloalkyl, cycloalkyl, aryl, alkoxy, alkoxyalkyl or a —C(R$^6$R$^7$)OH substituent, $R^6$ and $R^7$ are, independently of one another, a hydrogen atom, alkyl, haloalkyl, cycloalkyl or aryl, by reacting a mixture of an alkyne of the general formula IV $$R^5-C\equiv C-H \qquad (IV)$$

in which $R^5$ has the meanings stated above, and a carbonyl compound of the general formula V

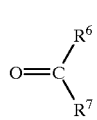

in which $R^6$ and $R^7$ have the meanings stated above, wherein the reaction takes place in the presence of a catalyst according to the invention.

In a preferred embodiment of the process according to the invention, the compounds prepared are those in which the radical $R^5$ is a hydrogen atom, alkyl or a —C(R$^6$R$^7$)OH substituent. The radicals $R^6$ and $R^7$ are preferably, independently of one another, a hydrogen atom or alkyl. The radicals $R^6$ and $R^7$ are, in particular, both hydrogen.

The alkyne of the formula IV employed to prepared compounds of the formula III in which $R^5$ is hydrogen is acetylene. The ratio of the molar quantities of acetylene and carbonyl compound of the formula V is then about 1:0.5 to about 1:1, so that essentially monoadducts result.

The alkyne of the formula IV employed to prepare compounds of the formula III in which $R^5$ is a —C(R$^6$R$^7$)OH substituent is likewise acetylene. The ratio of the molar quantities of acetylene and carbonyl compound of the formula V is then about 1:2 to 1:4, so that essentially bisadducts result.

The alkynol of the formula III is preferably propynol, 2-butyn-1-ol, 2-butyne-1,4-diol, 3-butyn-2-ol, 3-hexyne-2,5-diol, 3-pentyn-2-ol etc.

The invention further relates to a process for preparing aminoalkynes of the general formula VI

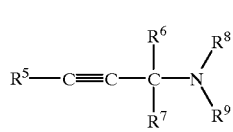

in which $R^5$, $R^6$ and $R^7$ have the meanings stated above, $R^8$ and $R^9$ are, independently of one another, a hydrogen atom, alkyl, haloalkyl, cycloalkyl, aryl or hydroxyalkyl, or $R^8$ and $R^9$ form, together with the nitrogen atom to which they are bonded, a 5- or 6-membered heterocyclic ring; by reacting a mixture of an alkyne of the general formula IV $$R^5—C\equiv C—H \qquad (IV)$$

in which
$R^5$ has the meanings stated above, a carbonyl compound of the general formula V

(V)

in which
$R^6$ and $R^7$ have the meanings stated above, and an amine of the general formula VII

(VII)

in which
$R^8$ and $R^9$ have the meanings stated above,
wherein the reaction takes place in the presence of a catalyst according to the invention.

The radicals $R^8$ and $R^9$ can form, together with the nitrogen atom to which they are bonded, a heterocyclic ring. Examples thereof are succinimido and phthalimido groups or an unsaturated or saturated, 5- or 6-membered heterocyclic ring which optionally contains another heteroatom selected from S and N, preferably N. Examples thereof which may be mentioned are: piperidinyl, piperazinyl and tetrahydropyrimidinyl groups.

In a preferred embodiment of the process according to the invention the compounds prepared are those in which the radical $R^5$ is a hydrogen atom, alkyl or a —$C(R^6R^7)OH$ substituent. $R^6$ and $R^7$ are preferably, independently of one another, a hydrogen atom or alkyl. The radicals $R^6$ and $R^7$ are, in particular, both hydrogen. It is further preferred for the radicals $R^8$ and $R^9$ to be, independently of one another, a hydrogen atom, alkyl or hydroxyalkyl. Suitable amines of the formula VII are then, for example, dimethylamine, diethylamine, di-n-propylamine, diisopropylamine, di-n-butylamine, diethanolamine, dipropanolamine etc.

The alkyne of the formula IV employed to prepare compounds of the formula VI in which $R^5$ is hydrogen is acetylene. The ratio of the molar quantities of acetylene and carbonyl compound of the formula V and amine of the formula VII is then about 1:0.5:0.5 to about 1:1:1, so that essentially monoadducts result.

The alkyne of the formula IV employed to prepare compounds of the formula VI in which $R^5$ is a —$C(R^6R^7)OH$ substituent is likewise acetylene. The ratio of the molar quantities of acetylene and carbonyl compound of the formula V and amine of the formula VII is then about 1:2:2 to about 1:4:4, so that essentially bisadducts result.

The aminoalkyne of the formula VI is preferably N,N-dimethylaminopropyne, N,N-diethylaminopropyne, N,N-dihydroxyethylaminopropyne, N,N-dimethylamino-2-butyne, N,N-diethylamino-2-butyne, N,N-dihydroxyethylamino-2-butyne, 5-(N,N-dimethylamino)-3-pentyn2-ol and, in particular, 5-(N,N-diethylamino)-3-pentyn-2-ol.

The alkynes of the formula I employed to prepare the catalysts according to the invention can in one embodiment correspond to the alkynes of the general formula IV employed in the catalyzed alkynylation or aminoalkylation reaction. In this case, the catalysts can generally be prepared immediately before the alkynylation or aminoalkylation, it being possible to dispense with isolation and, where appropriate, purification of the catalyst. It is preferred for the preparation of the catalyst and the subsequent reaction carried out therewith to take place in one reactor in a one-pot reaction.

In a further embodiment, however, the alkyne of the formula I employed to prepare the catalysts according to the invention can also differ from the alkynes of the formula IV employed in the catalyzed alkynylation or aminoalkylation reaction. This is, as described above, particularly important when acetylene is employed as alkyne for the alkynylation or aminoalkylation. In this case, an alkyne different from acetylene can be employed to prepare the catalyst, and the catalyst can, if desired, be prepared in a separate reactor. The resulting catalyst can be isolated and purified by conventional processes, e.g. by washing with water.

The invention further relates to the use of the catalysts according to the invention in alkynylation reactions and for preparing aminoalkynes by reacting an alkyne with a carbonyl compound and an amine.

The invention is illustrated in detail by the following, non-limiting examples.

EXAMPLES

1) Activation of an Unsupported Catalytic Composition Based on Malachite

A catalytic composition with a Bi content of 4% is prepared as described in DE-A-25 08 084.

377.5 g of formaldehyde (49% strength in water) are introduced under nitrogen into a 500 ml glass reactor with baffles and disk agitator, reflux condenser, temperature measurement, pH-electrode and feed for aqueous $NaHCO_3$ solution through an immersion tube, and heated to 70° C. and adjusted to pH 6.5 with $NaHCO_3$ solution (the temperature falls slightly during this). Heating is continued until the temperature in the reactor reaches 75° C., and then 9.7 g of malachite catalyst are suspended in 50 g of water and transferred into the reactor. Then 70.1 g of 3-butyn-2-ol (55% strength in water) are metered in continuously by an HPLC pump with stirring over a period of 4 h, during which the catalyst becomes dark in color over the course of some hours. If the pH falls below 6 during the activation reaction, 2% strength aqueous $NaHCO_3$ solution is added to compensate (total of 372 ml). The activation is completed after 8 h by slowly cooling to 25° C.

The catalyst is then removed by centrifugation and washed twice with water.

2) Activation of a Supported Catalytic Composition Based on Copper Oxide

The catalytic composition in the form of pellets is prepared as described in DE-A-26 02 418.

377.5 g of formaldehyde (49% strength in water) are introduced under nitrogen into a 500 ml glass reactor with baffles and disk agitator, reflux condenser, temperature measurement, pH-electrode and feed for aqueous $NaHCO_3$ solution through an immersion tube, and heated to 70° C. and adjusted to pH 6.5 with $NaHCO_3$ solution (the temperature falls slightly during this). Heating is continued until the temperature in the reactor reaches 75° C. (after about 15 minutes), and then 30 g of supported copper catalyst (pellets, about 15% CuO, 80% $SiO_2$ and 4% $Bi_2O_3$, diameter about 3 mm, length about 6 to 8 mm) are suspended in 50 g of water and transferred into the reactor. Then 70.1 g of 3-butyn-2-ol (55% strength in water) are metered in continuously by an HPLC pump with stirring over a period of 2.5 h. If the pH falls below 6 during the activation reaction, 2% strength aqueous NaHCO$_3$ solution is added to compensate (total of 100 ml). The activation is completed after 20 h by slowly cooling to 25° C. The catalyst is then filtered off and washed twice with water.

3) Activation of an unsupported catalytic composition based on malachite:

The procedure is analogous to the method of Example 1) but, in place of the 3-butyn-2-ol, 56.5 g of propargyl alcohol (55% strength in water) is metered in by an HPLC pump. A total of 350 ml of NaHCO$_3$ solution is added to adjust the pH.

4) Synthesis of diethylaminopentynol Using the Catalyst from Example 1

70.1 g (0.55 mol) of 3-butyn-2-ol (55% strength solution in water), 30.3 g of paraformaldehyde (1 mol) and 10 g of the activated malachite catalyst from Example 1 are introduced into a 250 ml stirred apparatus. After heating to 80° C., 73.1 g (1 mol) of diethylamine are added dropwise with stirring over the course of 1 h. The reaction mixture is then stirred at 80° C. for 22.5 h and is subsequently cooled slowly. The discharge is centrifuged and, after removal of the catalyst, worked up by distillation (yield: 85%). The catalyst can be employed anew after washing with water.

5) Synthesis of diethylaminobutynol Using the Catalyst from Example 3

56.1 g (0.55 mol) of propargyl alcohol (55% strength solution in water), 30.3 g of paraformaldehyde (1 mol) and 5.1 g of the activated malachite catalyst from Example 3 are introduced into a 250 ml stirred apparatus. After heating to 80° C., 73.1 g (1 mol) of diethylamine are added dropwise with stirring over the course of 1 h. The reaction mixture is then stirred at 80° C. for 22.5 h and is subsequently cooled slowly. The discharge is centrifuged and, after removal of the catalyst, worked up by distillation (yield: 92%). The catalyst can be employed anew after washing with water.

6) Synthesis of butynediol Using the Catalyst from Example 3

56.1 g (0.55 mol) of propargyl alcohol (55% strength solution in water), 101 g (1 mol) of formaldehyde (30% strength solution in water) and 5.1 g of the activated malachite catalyst from Example 3 are introduced into a 250 ml stirred apparatus. After the reaction mixture has been heated to 90° C. it is stirred at 90° C. for 22.5 hours, and then slowly cooled. The discharge is centrifuged and, after removal of the catalyst, analyzed by gas chromatography (30 m DB1 column, injector temperature 260° C., detector temperature 280° C., Hewlett Packard HP 580 90A apparatus, temperature program: initial temperature 80° C., heating rate 10° C./min, final temperature 280° C.) (yield 80%).

We claim:

1. A process for preparing a catalyst by activating a catalytic composition which comprises
   a) at least one metal of group IB or IIB or a compound thereof,
   b) where appropriate a carrier which comprises treating the composition with an alkyne of the general formula I $$R^1\text{—}C\equiv C\text{—}R^2 \qquad (I)$$

in which

R$^1$ is alkyl, cycloalkyl, aryl, hydroxyalkyl, haloalkyl, alkoxy or alkoxyalkyl, R$^2$ is a hydrogen atom, alkyl, cycloalkyl or aryl, and a carbonyl compound of the general formula II

(II)

in which

R$^3$ and R$^4$ are, independently of one another, a hydrogen atom, alkyl, haloalkyl, cycloalkyl or aryl.

2. A process as claimed in claim 1, wherein copper or a copper compound, preferably selected from copper oxide and malachite, is employed as component a).

3. A process as claimed in claim 1, wherein the catalytic composition also contains bismuth or a bismuth compound which is preferably selected from Bi$_2$O$_3$, (BiO)$_2$CO$_3$, Bi(NO$_3$)$_3$ and BiO(NO$_3$).

4. A process as claimed in claim 1, wherein a catalytic composition which comprises 10 to 20% by weight copper (II) oxide, 1 to 5% by weight bismuth oxide and 75 to 89% by weight silica is employed.

5. A process as claimed in claim 1, wherein a previously used, deactivated catalyst is employed as catalytic composition.

6. A process as claimed in claim 1, wherein an alkyne of the formula I in which R$^1$ is alkyl or hydroxyalkyl is employed.

7. A process as claimed in claim 1, wherein an alkyne of the formula I in which R$^2$ is a hydrogen atom or alkyl is employed.

8. A process as claimed in claim 1 wherein a carbonyl compound of the formula II in which R$^3$ and R$^4$ are, independently of one another, a hydrogen atom or alkyl, is employed.

9. A catalyst obtainable by a process as claimed in claim 1.

10. A process for preparing alkynols of the general formula III

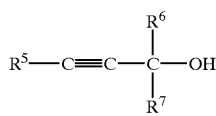

(III)

in which

R$^5$ is a hydrogen atom, alkyl, haloalkyl, cycloalkyl, aryl, alkoxy, alkoxyalkyl or a —C(R$^6$R$^7$)OH substituent, R$^6$ and R$^7$ are, independently of one another, a hydrogen atom, alkyl, haloalkyl, cycloalkyl or aryl, by reacting a mixture of an alkyne of the general formula IV $$R^5\text{—}C\equiv C\text{—}H \qquad (IV)$$

in which

R$^5$ has the meanings stated above, and a carbonyl compound of the general formula V

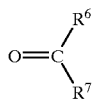
(V)

in which
R$^6$ and R$^7$ have the meanings stated above,
wherein the reaction takes place in the presence of a catalyst as claimed in claim 9.

11. A process for preparing aminoalkynes of the general formula VI

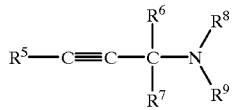
(VI)

in which
R$^5$, R$^6$ and R$^7$ have the meanings stated above,
R$^8$ and R$^9$ are, independently of one another, a hydrogen atom, alkyl, haloalkyl, cycloalkyl, aryl or hydroxyalkyl, or
R$^8$ and R$^9$ form, together with the nitrogen atom to which they are bonded, a 5- or 6-membered heterocyclic ring;
by reacting a mixture of an alkyne of the general formula IV

(IV)

in which
R$^5$ has the meanings stated above, a carbonyl compound of the general formula V

(V)

in which
R$^6$ and R$^7$ have the meanings stated above, and
an amine of the general formula VII

(VII)

in which
R$^8$ and R$^9$ have the meanings stated above,
wherein the reaction takes place in the presence of a catalyst as claimed in claim 9.

12. A process as claimed in claim 1, wherein the catalytic composition is treated under atmospheric pressure.

* * * * *

UNITED STATES PATENT AND TRADEMARK OFFICE
CERTIFICATE OF CORRECTION

PATENT NO. : 6,350,714 B1 Page 1 of 1
DATED : February 26, 2002
INVENTOR(S) : Boettcher et al.

It is certified that error appears in the above-identified patent and that said Letters Patent is hereby corrected as shown below:

<u>Title page,</u>
Item [87], PCT Pub. No.: "WO 98/35863" should be -- WO 99/28034 --;
PCT Pub. Date: "Aug. 20, 1998" should be -- June 10, 1999 --.
Insert the following priority information:
-- [30] Foreign Application Priority Data,
Dec. 2, 1997 (DE) ……….. 197 53 458 --.

Signed and Sealed this

Thirteenth Day of August, 2002

*Attest:*

JAMES E. ROGAN
*Attesting Officer* *Director of the United States Patent and Trademark Office*